United States Patent [19]
Lareau et al.

[11] Patent Number: 5,311,128
[45] Date of Patent: May 10, 1994

[54] EDDY CURRENT IMAGING SYSTEM USING SPATIAL DERIVATIVES FOR FLOW DETECTION

[75] Inventors: John P. Lareau, Granby, Conn.; David S. Leonard, Springfield, Mass.

[73] Assignee: Abb Amdata Inc., Windsor, Conn.

[21] Appl. No.: 905,202

[22] Filed: Jun. 26, 1992

Related U.S. Application Data

[63] Continuation of Ser. No. 545,487, Jun. 29, 1990, abandoned.

[51] Int. Cl.$^5$ ............... G01N 27/72; G01R 33/12
[52] U.S. Cl. ................... 324/233; 324/225; 324/237
[58] Field of Search ............ 324/233, 226, 236-243, 324/262, 225, 232; 364/481, 482, 550, 551.01

[56] References Cited

U.S. PATENT DOCUMENTS

| | | | |
|---|---|---|---|
| 4,470,122 | 9/1984 | Sarr | 364/559 |
| 4,555,664 | 11/1985 | David et al. | 324/225 |
| 4,755,753 | 7/1988 | Chern | 324/237 |
| 4,836,026 | 6/1989 | P'an . | |

OTHER PUBLICATIONS

E. J. Chern and A. L. Thompson, "Eddy Current Imaging For Material Surface Mapping" prepared in about Aug., 1986.

M. W. Kirby, J. P. Lareau, and D. S. Leonard, "Eddy Current Imaging of Aircraft Using Real Time Signal Processing" presented at the quantitative NDE conference in Jul., 1989.

*Primary Examiner*—Walter E. Snow
*Attorney, Agent, or Firm*—Ronald P. Kananen; John H. Mulholland

[57] ABSTRACT

An eddy current imaging system includes an eddy current sensing coil positioned proximate a workpiece for scanning the workpiece to produce a signal indicative of the integrity of the workpiece for regions in an x,y array of data. Such a signal may be a complex impedance signal representative of the amplitude and/or the phase of the signal. Two data processing techniques are disclosed for enhancing the display of a flay in the workpiece. The first includes the step of calculating a spatial derivative of the amplitude and/or phase indicative signal from the coil and providing an image of the spatial derivative to produce a C scan of the spatial derivative. The second includes the steps of determining the regions of maximum ascent and/or descent of the signal for regions in the scan and calculating an impedance plane trajectory from the data array of path points for displaying a reconstructed optimum signal independent of path pattern.

26 Claims, 3 Drawing Sheets

EDDY CURRENT IMAGING SYSTEM USING SPATIAL DERIVATIVES FOR FLOW DETECTION

This application is a continuation of application Ser. No. 07/545,487 filed Jun. 29, 1990, now abandoned.

BACKGROUND OF THE INVENTION

This invention relates to an eddy current imaging system for detecting flaws and for measuring property characteristics of materials. More specifically, this invention relates to a method of eddy current testing wherein a C scan of a spatial derivative of the amplitude and/or phase of a probe signal is provided in either real time, or for post processing analysis. Still more particularly, this invention relates to a method of determining scanned image sections with maximum ascent or descent of detected data and calculating an impedance plane trajectory for displaying an optimum flaw indication signal independent of scan pattern. Still more particularly, this invention relation to a method and apparatus for displaying a first spatial derivative of the instantaneous phase of the impedance of a signal generated by scanning a material with a selected eddy current sensing probe, in combination with a reconstructed optimum scan path calculated as a function of the regions of maximum ascent or descent of the data and an impedance plane trajectory.

A number of non-destructive testing techniques have been developed for detecting and displaying information regarding the structural integrity of a member. Such techniques have included eddy current testing methods for detecting flaws and measuring property characteristics. Systems utilizing such techniques are commercially available. In the case of flaw detection, the proximity of a material flaw to the test coil causes a change in the complex impedance of the coil which is detected and decoded by electronic circuitry in the system. Once the test parameters of frequency, coil size and orientation have been set, the response with an axisymmetric coil is nearly solely a function of the spatial relationship between the flaw and the test coil. Thus, for any set of surface coordinates x, y, the test response is calculable.

Most eddy current instruments provide either a strip chart or a complex impedance phasor plot of the detected data from the test coil to the instrument. In either case, the dynamic response of the test coil is a function of its position, as previously indicated, and the dynamics of the motion of scanning. Since both of these types of response are basically presentations of an instantaneous impedance of the coil as a function of time, the dynamic signal is thus a function of scan speed and scan direction for the test coil relative to the test specimen, and particularly with respect to a flaw. In general, therefore, the approach used for flaw detection is to scan in such a manner that coil motion is perpendicular to the major axis of a flaw. However, in the general case, this presumes some a oriori knowledge of the location and extent of the flaw orientation. An advantage of this scanning motion is that the maximum contrast signal, i.e. one having the highest signal to noise ratio, results from the perpendicular intersect of coil path and flaw outline which thus facilitates flaw detection.

Prior systems have also included a display of the complex impedance of the signal from the test coil as a function of the position of the coil rather than as a function of time. Such a C scan display, as such a display is commonly referred to, usually depicts the amplitude of a component of the impedance, although some prior art systems have also displayed phase in a C scan mode. In either case, the actual spatial position is usually inferred from the temporal data using an assumption of constant scan velocity and the plot of either signal amplitude or signal phase versus x-y position is indicated.

In particular, an instrument available from Zetec referred to in the art as a MIZ-18 instrument produces C scan plots of amplitude of the test signal from the coil, or a time derivative of the amplitude of the test signal from the coil.

However, the interpretation of such signals is still based on spatial information, even though the amplitude, phase, and time derivatives of the amplitude are useful. Such systems which use time derivatives are dependent on an assumption of constant velocity, as noted above, to deduce the spatial relationship of a detected flaw, especially in the presence of background noise. By using the assumption of constant velocity to deduce position, it has been determined in another context that the image sections with the maximum ascent or descent of the test signal is a significant method for detecting subsurface flaws.

Thus, it has remained a significant problem in this art to provide a system in which the mechanical scanning system and the data acquisition parameters can be determined somewhat independently so that the scanning can be done in any convenient format such as a meander pattern or by raster scanning without sacrificing the quality of the test results. As a practical example where such an approach would be beneficial is the inspection of a structure such as an airplane wing. Mechanically, the easiest way to scan the wing is in a meander scan along the length of the wing with incremental indexing steps at the end of each stroke. Typically, flaws would emanate from rivet holes at any arbitrary orientatin and the above scan would be expected to miss some flaws due to poor signal to noise ratio conditions at certain flaw orientations. With such a scan pattern system, the locally optimum scan direction could be determined and this scan synthesized from the available date. In this manner, the optimum mechanical and signal criteria can be simultaneously satisfied.

Accordingly, it has also remained a significant problem in this art to provide a reconstructed optimum scan path based on scan data wherein the optimum path traverses a flaw edge in a given pixel at a right angle, or near thereto, for maximizing the signal-to-noise ratio.

BRIEF SUMMARY OF THE INVENTION

Directed to achieving the forgoing objects and addressing the problems noted for this art, the invention relates to a method and program apparatus for contrast imaging a workpiece with an eddy current imaging means including an eddy current sensing coil positioned proximate the workpiece and traversing said workpiece in a pattern. Thus, the workpiece is scanned to produce a signal indicative of the impedance of said workpiece proximate said eddy current sensing coil. The method includes the steps of providing a signal from the impedance indicative signal representative of the amplitude and/or phase of the signal; calculating a spatial derivative of said amplitude and/or phase indicative signal; and providing an image of the spatial derivative.

Preferably, the step of providing an image of said spatial derivative includes the step of producing a C scan of the spatial derivative.

If desired, the step of producing the C scan may be performed in approximately real time relative to said scan of said workpiece.

Another significant feature of the invention relates to determining an optimum calculated scan path independent of the actual scan. This second feature of the invention includes a method and apparatus for receiving scan signals from an eddy current sensing coil; determining the maximum ascent and/or descent of the signal values of the scanned image sections, preferably on a pixel-by-pixel basis, using spatial operators preferably gradients, and detecting true flaw signals therefrom in the presence of background regions of maximum ascent and/or descent are used for calculating an impedance plane trajectory from a data array of path points and the maximum descent region. The amplitude of the gradient is a primary indicator of the presence of a flaw and the direction of the maximum gradient is used to determine the optimum path for signal reconstruction. From these calculations, the optimum signal path is determined independent of scan pattern. In practical terms, the calculated scan pattern is at or near a right angle to the flaw outlined to maximize contrast.

The foregoing features may also be used in combination.

DETAILED DESCRIPTION OF THE PREFERRED EMBODIMENT

Figure 1:
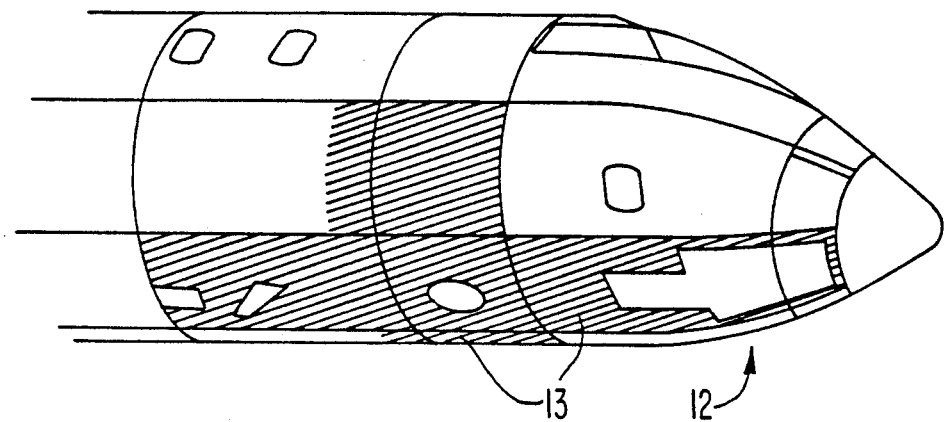
FIG. 1 shows a representative array of areas on an aircraft that are tested for corrosion, to which the subject invention is applicable.

FIG. 1 shows a portion of a fuselage of an aircraft 12 having typical and representative areas 13 that are inspected for corrosion or cracks to detect potential for component failures. Usually, a structural failure in an aircraft 12 is caused by fatigue cracking, corrosion, or a combination of both. To non-destructively evaluate such aircraft, it is considered desirable to provide a reliable technique to detect surface and subsurface cracking on the order of 0.06 inch (1.5 mm) long and corrosion wall loss of about 10% to satisfy safety concerns. The invention can thus be applied, by way of example, for non-destructive evaluation (NDE) of the surfaces of an aircraft; however, it is not limited to this field of use. It may also be used for vessel evaluations, by way of example.

Figure 2:
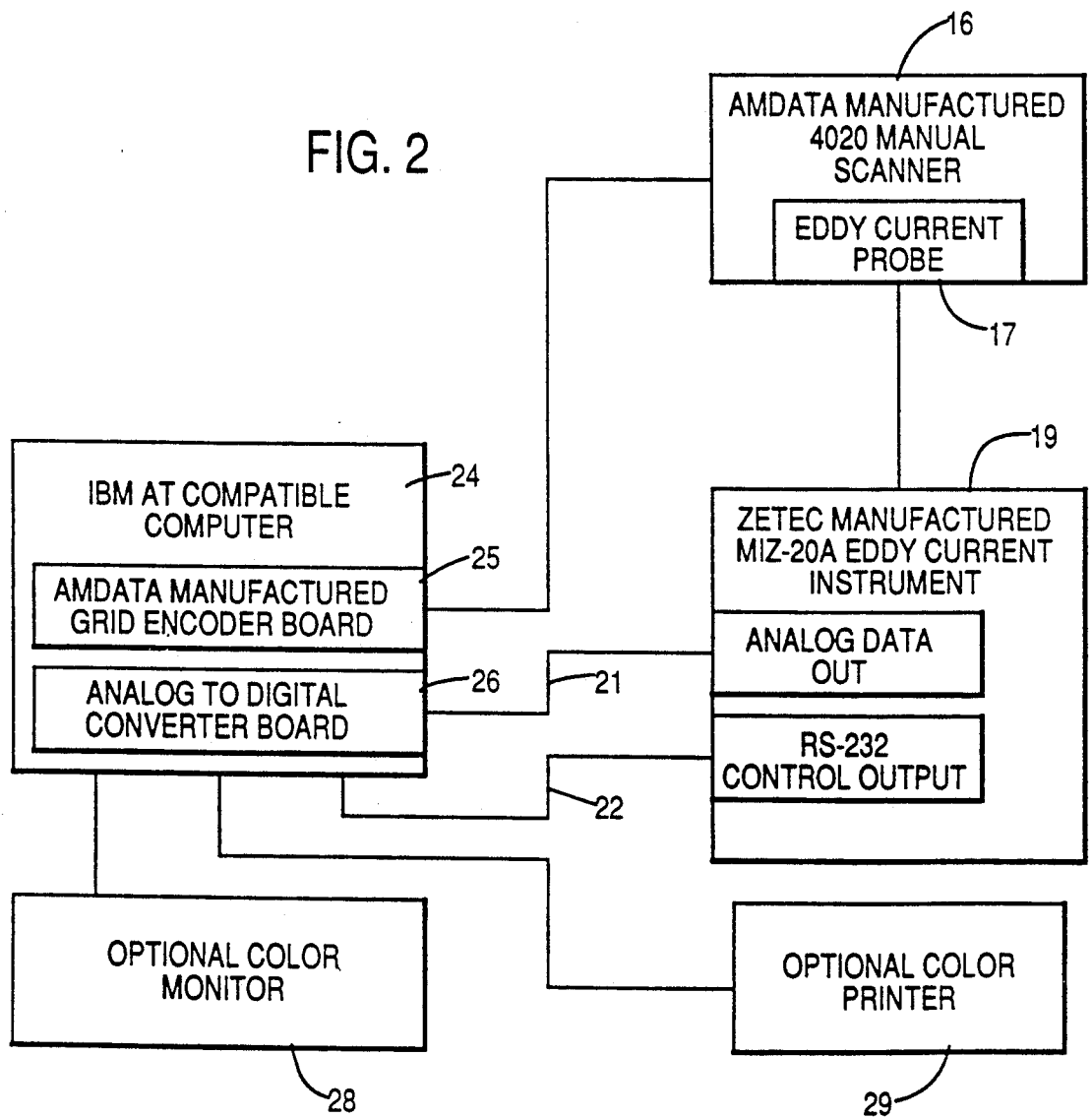
FIG. 2 is a block diagram of a representative apparatus for practicing the invention.

FIG. 2 is a representative block diagram of a system 15 providing hardware for incorporating the principles of the invention in a laboratory environment. The system 15 includes a manual scanner 16 for securing an eddy current probe 17 for traversing an area of scan. A suitable manual scanner is available from the assignee of this invention under Model No. 4020. In a commercial environment, a number of scanning devices can be used, including those which scan a test sample manually, automatically according to a predetermined x-y scan, such as a raster scan, or by meander scanning. The choice of scanner is somewhat determined by the nature of the test sample.

Figure 3:
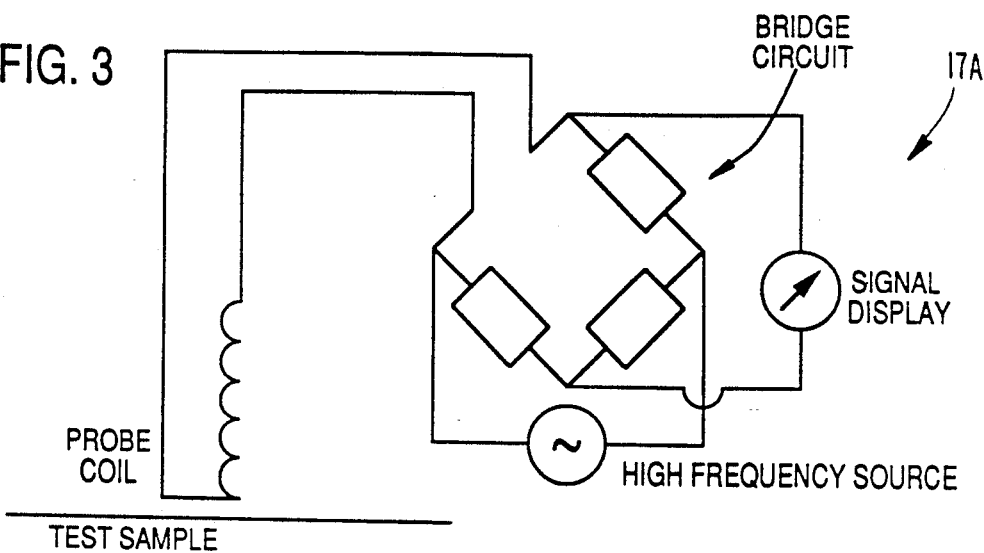
FIG. 3 shows an absolute probe used for corrosion mapping using a probe coil adjacent a test sample to produce a signal for the system of the invention.
Figure 4:
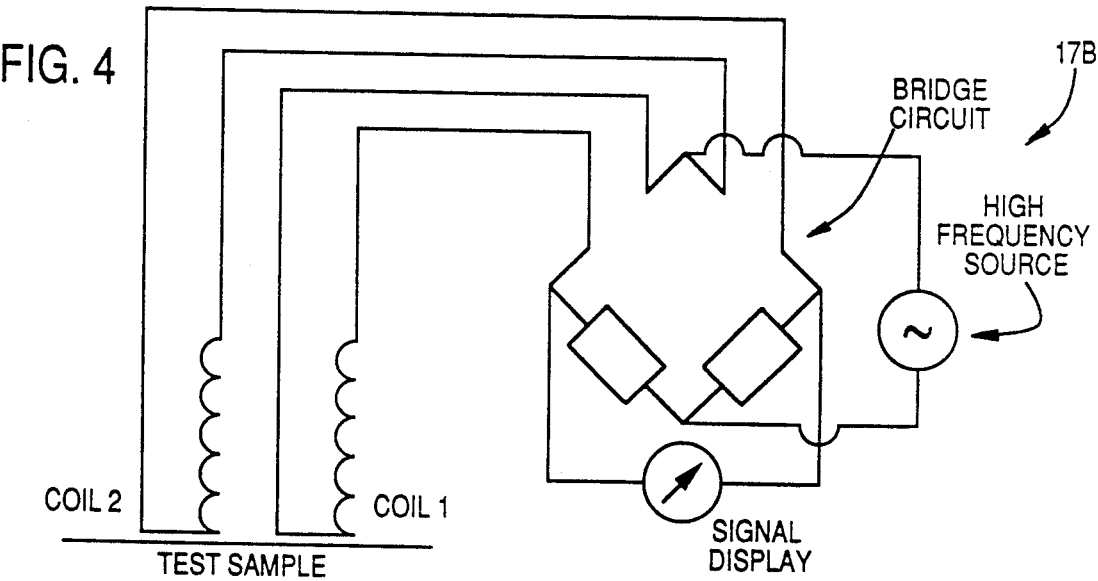
FIG. 4 shows a differential probe used for crack detection using a pair of probe coils adjacent a test sample to produce a signal for the system of the invention.
Figure 5:
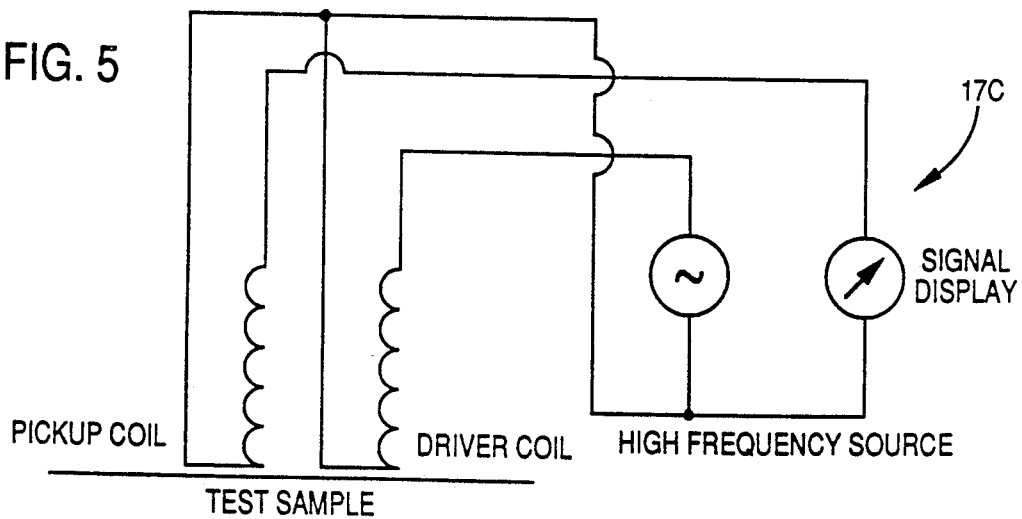
FIG. 5 shows a driver/pickup probe used for crack detection where the sensitivity of a differential probe is inadequate.

Suitable eddy current test probes 17A, 17B and 17C are representatively shown in FIGS. 3 to 5 to provide an analog output signal representative of the phase and amplitude of the test signal detected by the probe 17 from the test sample. The analog output from the eddy current probe 17 is provided to an eddy current instrument 19, such as a Zetec Model No. MIZ-20A, suitable for receiving the output from the eddy current probe. The eddy current probe 17 is a two axis encoding device proving the spatial information necessary to plot the analog data 21 as well as generate the synchronizing pulses 22 for acquiring data on a preset grid. Typically, the data 21, 22 is obtained in increments of one quarter of the coil diameter.

The eddy current instrument 19 used in the system 15 is a single frequency instrument with an operating range from about 100 Hz to about 2 MHz. Alternatively, a four frequency instrument can be used when multiparameter mixing is beneficial.

The system 15 includes a computer, such as an IBM AT compatible computer 24, connected to an Amdata encoder board 25 which in turn is connected to the manual scanner 16. Data collection in an x,y mode continues for each scan of the scanner 16 for coordination with the digitized data representative of the analog scan signals 21, 22 through the analog to digital converter board 26. To display the data upon command in real time, or upon processing, a color monitor 28 and a color printer 29 are provided.

The system 15 is configured to measure a number of quantities as a function of the coil position 17. Among those quantities are the in phase impedance amplitude, and the quadrature impedance amplitude of the test sample according to the analog signal generated by the probe. In addition, the system 15 is programmed to determine through near real time calculations, the following quantities: (1) impedance vector magnitude; (2) impedance vector phase; and (3) various orders of spatial derivatives of the impedance vector magnitude and the impedance vector phase. The displays may be on strip charts or on complex impedance phasor plots.

Figure 6:
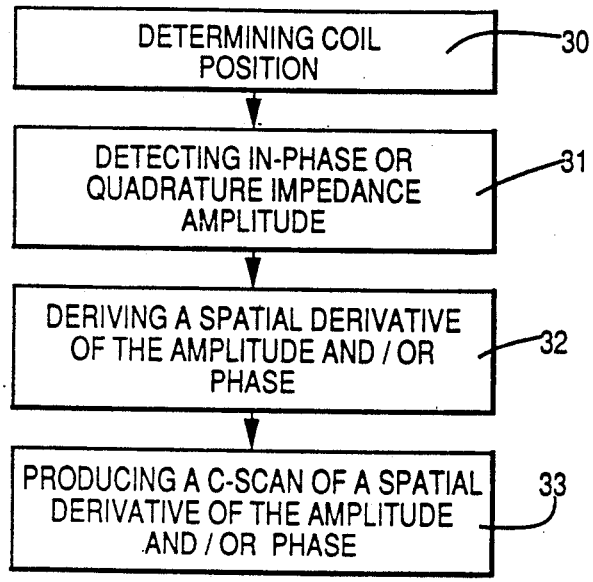
FIG. 6 is an illustration of a flow routine illustrating one feature of the invention.

A first and significant feature of the invention is that the instantaneous phase of the impedance, i.e. a first spatial derivative of the impedance is displayed. Thus, FIG. 6 shows a subroutine programmed into the apparatus 15 of FIG. 2 to produce a C scan of a spatial derivative of the amplitude and/or phase of the coil signal coordinated with the coil position of the eddy current coil 17. Thus, in step 30, the position of the coil 17 is determined by the encoder board 25 cooperating with the scanner 16. The in-phase or quadrature impedance amplitude is detected from the analog signal output by the coil probe selected, as in step 31. From the data of step 31, a spatial derivative of the amplitude and/or phase of the signal is derived, as in step 32, thus enabling the production of a C scan of the derived spatial derivative.

Display of the spatial derivative as described reduces a major component of the signal noise and improves flaw detection. Indeed, prior systems display total signal phase signals including noise which reduces erroneous readings. Thus, flaw detection is improved.

Figure 7:
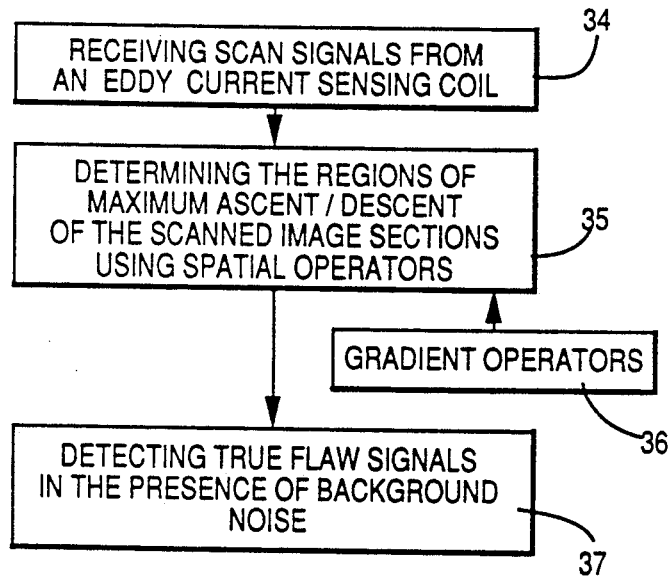
FIG. 7 is another illustration of a flow routine illustrating the steps of determining the maximum ascent/descent of received data for synthesizing a calculated flaw path independent of the actual traversal path.
Figure 8:
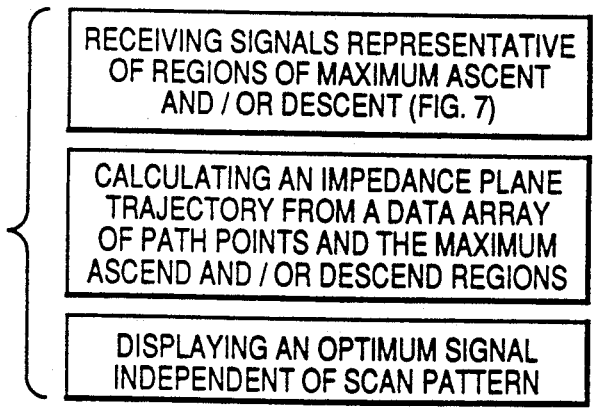
FIG. 8 illustrates the step of using the calculated flaw path with a step of calculating an impedance plane trajectory for handling data for displaying optimum signal strength independent of path position or scan pattern.

A second significant feature of the invention is shown by the subroutines of FIGS. 7 and 8. Since the eddy current test signal at any given point in the scan is independent of the scan path, the storage of data with precise location information in the system 15 of FIG. 2 allows for the post processing calculation of dynamic signals for an arbitrary scan path. Although the instantaneous signal from the test coil 17 is path independent, the dynamic signal is path dependent and is the usual form of signal which is most readily used for interpretation of results for crack or flaw detection. Indeed, the signal to noise ratio, or the image contrast, can be enhanced by proper selection of the scan path, whether real or reconstructed.

Accordingly, a routine is provided for automatically determining the optimum path which is calculated based on the direction of maximum ascent/descent by algorithms used to determine maximum gradients in signal amplitudes of the signals from the test coil 17 of the eddy current instrument 19. Both the gradient magnitude and direction are determined. With this method, the most efficient scan path for mechanical considerations, typically, a rectilinear scan, can be used to acquire data while any scan path can be synthesized from the recorded data to optimize flaw detection, even without a oriori knowledge of the flaw orientation. This provides a significant second advantage for the system.

FIG. 7 thus shows an initial subroutine for determining the optimum calculated path by first determining the direction of the maximum ascent/descent of the scan image section using spatial operators, usually gradient operators. This technique permits location of a flaw or crack which then can be used to determine the optimum path for scanning that flaw or crack in a direction at or nearly perpendicular to the flaw or crack. The optimum path is a reconstructed one from the data of the original scan. Thus, in FIG. 7, a step 34 of receiving the scanned signals is followed by the mathematical step 35 of determining the maximum ascent/descent of the scanned image sections, preferably in a pixel-by-pixel basis, using spatial operators, and in particular gradient operators, as shown in step 36. The step 37 is the step of determining true flaw signals in processing the data according to the subroutine of FIG. 8.

The subroutine of FIG. 8 permits a reconstruction of a signal trace by synthesizing an arbitrary scan path along the direction of maximum ascent/descent. The initial step 40 in the subroutine is a step of receiving signals representative of regions of maximum ascent/descent, as in FIG. 7 as discussed above. Those signals are used to calculate an impedance plane trajectory from the data array, as in step 41. In the data array from which the gradient was calculated in accordance with FIG. 7, the signal is only a function of position relative to a flaw and is path independent for symmetric coil designs of the type shown in FIGS. 3 to 5. However, the optimum signal that an analyst would use for a determination of flaw/no flaw is highly path dependent. Thus, the signal generated in the direction of the maximum gradient provides the optimum signal to noise ratio and is the best estimate of the true flaw characteristics. Accordingly, by the steps of FIG. 8, a display of the optimum signal independent of the scan pattern used to acquire the data is possible, as shown in step 42. There are significant practical advantages of analyzing data as described herein. First, the mechanical scanning system and the data acquisition parameters can be determined somewhat independently. Second, since an eddy current scanning system works best when the sensing coils 17 traverse a flaw at right angles, a optimum path can be developed through calculations, whether or not the original scanning was done in a raster scanning or a meander scanning mode, without sacrificing the quality of the test results.

When applied to an aircraft structure, such as in FIG. 1, for example, a scan produces data which are analyzed for the maximum regions of ascent/descent. When applied to a situation involving cracks radially emanating from a rivet, for example, the analysis produces a optimum calculated path which is circular to intersect the crack at about a right angle.

While a preferred embodiment of the invention has been illustrated, it will be apparent to those skilled in the art that various modifications and changes may be made thereto without departing from the spirit and scope of the invention as defined in the appended claims.

We claim:

1. A method for contrast imaging a workpiece with eddy current imaging means including an eddy current sensing coil positioned proximate said workpiece by traversing said workpiece in an arbitrary pattern independently of velocity or direction, thus to scan said workpiece and produce a signal indicative of the impedance of said workpiece proximate said eddy current sensing coil and the location of said sensing coil, said method including:

providing a signal from said impedance indicative signal representative of the amplitude of said signal for selected scan positions;

calculating a spatial derivative in one or more dimensions of said amplitude indicative signal;

providing an image of said spatial derivative for said selected scan positions; and recording true sensor position for said selected scan positions.

2. The method as set forth in claim 1 wherein the step of providing an image of said spatial derivative includes the step of producing a C scan of said spatial derivative.

3. The method as set forth in claim 2 wherein the step of producing said C scan is performed in approximately real time relative to said scan of said workpiece.

4. The method as set forth in claim 1, including a step of storing said signal, wherein said calculating step is performed at a time later than said scan of said workpiece.

5. A method of displaying a contrast image of a flaw in a workpiece which is scanned in an arbitrary pattern independently of velocity or direction by an eddy current coil to produce a quadrature impedance amplitude indicative signal, comprising the steps of:

deriving a spatial derivative in one or more dimensions of said amplitude indicative signal for selected positions in said arbitrary pattern; and producing said contrast image by displaying said spatial derivative in one or more selected dimensions.

6. The method as set forth in claim 5 wherein said spatial derivative is displayed as a C scan of said flaw.

7. The method for contrast imaging a workpiece with eddy current imaging means including an eddy current sensing coil positioned proximate said workpiece and traversing said workpiece in a pattern, thus to scan said workpiece ad produce a signal indicative of the impedance of said workpiece proximate said eddy current sensing coil for each scanned position of interest, said method including:
  determining for said signal indicative of the impedance of said workpiece the maximum rate of change of the scanned image sections by spatial operators; and
  detecting true flaw signals in the presence of background noise form said regions of maximum rate of change.

8. The method as set forth in claim 7 further including the steps of:
  calculating an impedance plane trajectory from a data array of path points and the direction of maximum rate of change regions; and
  displaying an optimum signal independent of scan pattern of said workpiece.

9. The method as set forth in claim 7 wherein the step of using spatial operators includes the step of using gradient operators.

10. A method for contrast imaging a workpiece, comprising the steps of;
  scanning said workpiece with an eddy current imaging means including an eddy current sensing coil positioned proximate said workpiece to produce data representative of the integrity of said workpiece in an x, y group;
  determining from said x, y group of data the regions of maximum rate of change of the scanned image sections;
  calculating from said x, y group of data and the maximum rate of change of the scanned image sections an impedance plane trajectory; and
  determining an optimum signal independent of an original scan pattern.

11. The method as set forth in claim 10 wherein the step of determining the maximum rate of change includes the step of using spatial operators.

12. The method as set forth in claim 11 where the step of using spatial operators includes the step of using gradient operators including both magnitude and direction of the gradient vector.

13. The method as set forth in claim 10 further including a step of detecting true flaw signals in the present of background noise after determining the regions of maximum rate of change.

14. The method as set forth in claim 1 wherein said impedance indicative signal which is provided as representative of the amplitude of said signal for selected scan positions is a multi-frequency, multi-parameter signal.

15. The method as set forth in claim 1, wherein said eddy current imaging means produces a signal indicative of the impedance of said workpiece proximate said eddy current sensing coil an the location of said sensing coil at one or more excitation frequencies, wherein said impedance indicative signal is indicative of the amplitude of a signal frequency/signal parameter, or for a multi-frequency/multiple parameter signal for said signal.

16. The method as set forth in claim 7, wherein the step of determining includes a step of determining both maximum gradient in amplitude and direction for said signals.

17. The method as st forth in claim 16 further including a step of flaw detection along an optimum path perpendicular to said gradient.

18. The method as set forth in claim 7 further including a step of reconstructing a signal trace by synthesizing an arbitrary scan path along the direction of maximum rate of change.

19. The method as set forth in claim 10, wherein the step of determining includes a step of determining both maximum gradient in amplitude and direction for said signals.

20. The method as set forth in claim 10 further including a step of reconstructing a signal trace by synthesizing an arbitrary scan path along the direction of maximum rate of change.

21. The method as set forth in claim 1, wherein the impedance indicative signal is also representative of a phase of said signal for selected scan positions and spatial derivatives are also calculated for said phase indicative signal.

22. A method for contrast imaging a workpiece with eddy current imaging means including an eddy current sensing coil positioned proximate said workpiece by traversing said workpiece in an arbitrary pattern independently of velocity or direction, thus to scan said workpiece and produce a signal indicative of the impedance of said workpiece proximate said eddy current sensing coil and the location of sensing coil, said method including:
  providing a signal from said impedance indicative signal representative of the phase of said signal for selected scan positions;
  calculating a spatial derivative in one or more dimensions of said phase indicative signal;
  providing an image of said spatial derivative for said selected scan positions; and
  recording true sensor position for said selected scan positions.

23. The method as set forth in claim 5, wherein said eddy current also produces an in phase indicative signal and said step of deriving said spatial derivative derives a spatial derivative of said phase indicative signal.

24. A method of displaying a contrast image of a flaw in a workpiece which is scanned in an arbitrary pattern independently of velocity or direction by an eddy current coil to produce an in phase indicative signal, comprising the steps;
  deriving a spatial derivative in one or more dimensions of said phase indicative signal for selected positions in said arbitrary pattern; and
  producing said contrast image by displaying said spatial derivative in one or more selected dimensions.

25. The method as set forth in claim 22 wherein said impedance indicative signal which is provided as representative of the phase of said signal for selected scan positions in a multi-frequency, multi-parameter signal.

26. The method as set forth in claim 22, wherein said eddy current imaging means produces a signal indicative of the impedance of said workpiece proximate said eddy current sensing coil and the location of said sensing coil at one or more excitation frequencies, wherein said impedance indicative signal is indicative of the phase of a signal frequency/signal parameter, or for a multi-frequency/multiple parameter signal for said signal.

* * * * *